(12) United States Patent
Chen et al.

(10) Patent No.: US 9,370,310 B2
(45) Date of Patent: Jun. 21, 2016

(54) DETERMINATION OF CELLULAR ELECTRICAL POTENTIALS

(75) Inventors: Yao Chen, Shanghai (CN); Kai Thomenius, Clifton Park, NY (US); Yongsheng Yang, Shanghai (CN); Fei Teng, Shanghai (CN); Yong Zhang, Shanghai (CN); Jian Zhou, Shanghai (CN); Joel Xue, Germantown, WI (US)

(73) Assignee: GENERAL ELECTRIC COMPANY, Niskayuna, NY (US)

( * ) Notice: Subject to any disclaimer, the term of this patent is extended or adjusted under 35 U.S.C. 154(b) by 2393 days.

(21) Appl. No.: 11/654,922

(22) Filed: Jan. 18, 2007

(65) Prior Publication Data
US 2008/0177192 A1 Jul. 24, 2008

(51) Int. Cl.
*A61B 5/0402* (2006.01)
*A61B 6/00* (2006.01)
*A61B 5/00* (2006.01)
*A61B 8/08* (2006.01)

(52) U.S. Cl.
CPC .......... *A61B 5/0402* (2013.01); *A61B 5/04028* (2013.01); *A61B 5/7278* (2013.01); *A61B 6/503* (2013.01); *A61B 5/725* (2013.01); *A61B 5/742* (2013.01); *A61B 8/0883* (2013.01)

(58) Field of Classification Search
USPC ......... 600/301, 407, 410, 411, 425, 427, 509, 600/523–525, 547
See application file for complete search history.

(56) References Cited

U.S. PATENT DOCUMENTS

| | | | | |
|---|---|---|---|---|
| 4,961,428 A * | 10/1990 | Nikias et al. | | 600/512 |
| 5,151,856 A * | 9/1992 | Halmann et al. | | 600/508 |
| 5,634,469 A * | 6/1997 | Bruder et al. | | 600/512 |
| 5,692,907 A | 12/1997 | Glassel | | |
| 6,772,004 B2 | 8/2004 | Rudy | | |
| 6,856,830 B2 * | 2/2005 | He | | 600/513 |
| 6,975,900 B2 | 12/2005 | Rudy et al. | | |
| 7,016,719 B2 | 3/2006 | Rudy et al. | | |
| 7,841,986 B2 * | 11/2010 | He et al. | | 600/508 |
| 2003/0018457 A1 * | 1/2003 | Lett et al. | | 703/11 |
| 2003/0236466 A1 * | 12/2003 | Tarjan et al. | | 600/508 |
| 2005/0256415 A1 * | 11/2005 | Tan et al. | | 600/509 |

FOREIGN PATENT DOCUMENTS

WO 0198935 12/2001

OTHER PUBLICATIONS

Bommel et al. "Boundary Element Solution of Biomagnetic Problems", IEEE Trans. Magn. MAG-29, 1993, pp. 1397-1398.*

\* cited by examiner

*Primary Examiner* — Eugene Wu
(74) *Attorney, Agent, or Firm* — Fletcher Yoder, P.C.

(57) ABSTRACT

A method is provided for determining cellular electrical potentials using a state estimator. The state estimator is generated using at least an electrical source model and an electrical conduction model. One or more parameters or states of the state estimator are adjusted based on a measured electrocardiographic and/or a measured body-surface-potential signal. The electrical potential of one or more cells is determined based on the one or more adjusted parameters or states. In one aspect of the present technique, one or more representations of an organ comprising the one or more cells is generated such that the electrical potential or its deriving characteristic of the one or more cells is visually indicated.

28 Claims, 7 Drawing Sheets

DETERMINATION OF CELLULAR ELECTRICAL POTENTIALS

BACKGROUND

The invention relates generally to medical monitoring and diagnosis and, in particular, to the mapping of electrocardiographic information.

In the field of medicine, the acquisition of diagnostic and/or monitoring data from a patient has become more common as systems designed to collect such data have become more accessible and their use more routine. One example of such diagnostic and/or monitoring data is electrocardiographic (ECG) data which represents cardiac electrical activity associated with the muscular pumping activity of the heart. The ECG data is collected by numerous contacts or leads disposed on the skin of a patient and generally represents the underlying electrical activity of the patient's heart. For example, aberrations in the activity of the heart may generate characteristic waveform patterns or traces that a trained clinician can recognize.

However, the ECG data may contain more information than is evidenced in a simple, aggregate waveform that is typically associated with ECG measurements. For example, it may be desirable take advantage of structural or anatomical models or information in conjunction with the ECG data to provide insight into the interplay between cardiac structure and electrical activity.

BRIEF DESCRIPTION

The present technique is generally directed to the use of anatomical data of a patient in conjunction with electrical data for the patient, such as electrocardiographic data or body-surface-potential data. In particular, the present technique provides information about the condition of a heart by constructing an electrical activity mapping of the heart using a state estimator that, based on provided, measured electrical data and anatomical data, can be used to estimate parameters or states associated with myocardial cell electrical potentials. Based on these estimated parameters or states of the model, myocardial cell electrical potentials can be estimated in a dynamic fashion. The myocardial cell electrical potentials may be mapped to anatomical image data of the heart to generate surface or volumetric representations of the heart that visually reflect the myocardial cell electrical potentials and changes in the electrical potentials over the course of a heart beat.

A method is provided for determining cellular electrical potentials. The method includes the act of generating a state estimator using at least an electrical source model and an electrical conduction model. One or more parameters or states of the state estimator is adjusted based on at least one of a measured electrocardiographic signal or a measured body-surface-potential signal. The electrical potential of one or more cells is determined based on the one or more adjusted parameters or states. Corresponding diagnostic systems and application instructions on computer-readable media are also provided.

DRAWINGS

These and other features, aspects, and advantages of the present invention will become better understood when the following detailed description is read with reference to the accompanying drawings in which like characters represent like parts throughout the drawings, wherein.

DETAILED DESCRIPTION

Research and treatment of cardiac disease may benefit from being able to model the related electrical phenomena associated with heart activity, such as electrocardiographic (ECG) data or body-surface-potential (BSP) measurements. In general, modeling or representing ECG or BSP data involves two types of models, an electrical activity source model of the heart and an electrical conduction model of the heart and torso. The electrical conduction model may generally be represented as $$Y = A \cdot X \qquad (1)$$

where Y denotes the measured ECG or BSP signal at the skin, X denotes the corresponding electrical potential or activation of the heart at a cellular level, i.e., the cardiac electrophysiological activity, and A denotes the parameters of the model correlating X and Y. The forward problem of solving for Y in this equation is generally straight-forward. The inverse problem of solving for X, however, may be problematic due to the sensitivity of the direct solution, $X = inv(A'A)(AY)$, to measurement noise and model error. To address this problem, regularization may be added by applying constraints on the solution, however such an approach may reduce the capability of identifying heart abnormalities using the solution since indications of the abnormality may be reduced or eliminated by the constraints. In addition, existing approaches typically provide sample-by-sample solutions, but fail to account for periodic behavior within the heart beat cycle, i.e., electrical behavior or phenomena that is correlated in time to certain portions of the heart beat cycle. The present technique addresses some or all of these failings by leveraging the electrical source model to address dynamic characteristics within the heart beat cycle. In one embodiment, an extended Kalman filter is used to dynamically characterize and adjust the model parameters of the electrical source model such that the simulated ECG and/or BSP correspond with or match the respective ECG and/or BSP measurements. In such an embodiment, the inverse problem solution is an indirect solution that is calculated using the adjusted model parameters.

Figure 1:
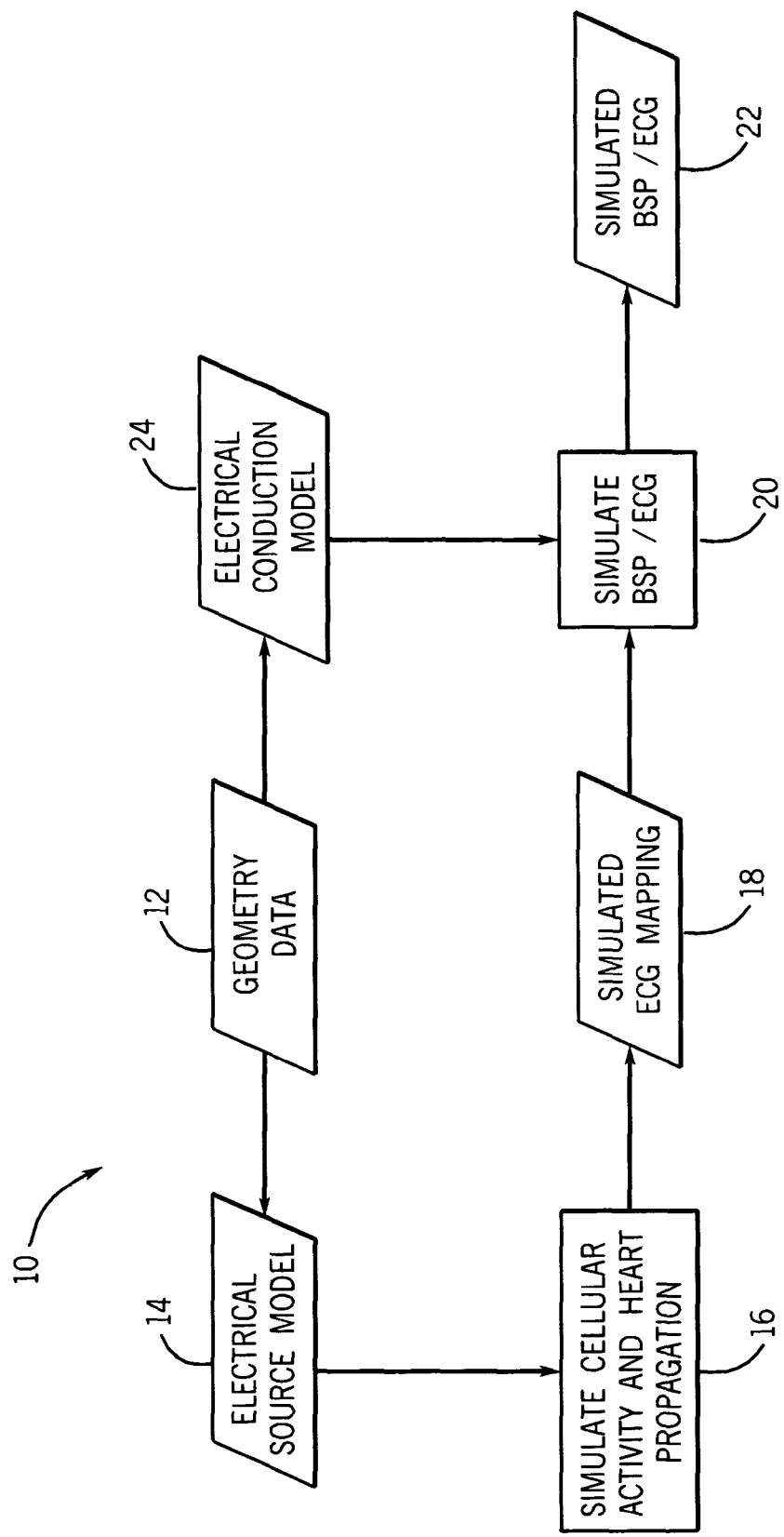
FIG. 1 illustrates an exemplary technique for generating simulated body surface potential and/or ECG data, in accordance with one aspect of the present technique.

For example, for the purpose of explanation a simplified diagram illustrating the forward problem 10 of simulating an ECG and/or BSP measurement for a patient is provided in FIG. 1. In this simplified example, geometry data 12 for a patient is provided that represents the three-dimensional geometry or actual anatomical structure of the heart and torso of the patient. For example, the geometry data 12 of the patient's heart and torso may be provided as a three-dimensional volume or image derived using computer tomography (CT), magnetic resonance imaging (MRI) or ultrasound techniques, or other imaging techniques suitable for deriving and depicting the anatomical three-dimensional structure of the heart and torso. In addition, an electrical source model 14 is provided that describes the electrical activity of the heart. The electrical source model 14 may include or incorporate additional models, such as a cellular electrical or electromechanical model and/or a heart electrical or electromechanical propagation model. In one embodiment, the electrical source model 14 models the electrical activity of each cell of the patient's heart and a propagation sequence among the patient's heart cells. In an exemplary embodiment, the electrical source model 14 models electrical activity of the patient's heart for a given disease state or models the electrical activity of the patient's heart in the absence of such a disease state.

In solving the forward problem, the electrical source model 14 and the geometry data 12 are used to simulate and map (block 16) the electrical activity of the heart for the patient, thereby generating a simulated ECG mapping 18 for the heart. For example, in an implementation where the electrical source model 14 represent the surface or volume electrical activity of a healthy heart, this electrical activity may be mapped to the specific anatomy, i.e., geometry 12, of the patient's heart to provide an anatomically, i.e., geometrically, precise representation of the activity of a healthy heart down to the cellular level. The result of such a mapping process is a simulated ECG mapping 18 of the electrical activity of the patient's heart in the absence of disease. Conversely, various disease or abnormality states may be represented or indicated in the electrical source model 14 such that the electrical source model 14 represents the aberrant electrical activity of the diseased or abnormal heart. The electrical source model 14 of the diseased or abnormal heart may then be simulated (block 16) and mapped to the patient's heart geometry 12 to provide a simulated ECG mapping 18 that is an anatomically precise representation of the activity of the diseased or abnormal heart down to the cellular level.

The simulated ECG mapping 18 representing the electrical activity of the heart in the context of the patient's heart geometry may be used to simulate (block 20) the BSP or ECG as it would be measured on the patient's skin, i.e., after conduction of the electrical signals through the patient's torso. To generate these simulated BSP or ECG values 22, which may be provided as waveforms or traces, an electrical conduction model 24 is used in conjunction with the simulated ECG mapping 18. As will be appreciated by those of ordinary skill in the art, the electrical conduction model 24 models the conduction of cardiac electrical potentials through the heart, the torso or other body region being modeled. As noted above, the electrical conduction model may take the form of $Y=A \cdot X$, where Y is the measured body surface potential (as a BSP or ECG measurement) measured at a location on the skin at a given time, X is the cardiac electrophysiological activity at a given cardiac cell or group of cells forming an anatomical structure or region of the heart at the given time, and A is a constant representing the conductive properties between the cardiac cell whose electrical potential is modeled by X and the surface location where the potential is to be measured as Y.

In this way, the electrical properties of a healthy or diseased heart may be modeled with geometric precision and the resulting measurements that would be observed at the body surface of the patient may in turn be simulated with precision. Likewise, the electrical source model 14 may be modified to reflect different states of cardiac health, i.e., different diseases, disease states, and/or abnormalities. These various electrical source models 14, along with the patient specific cardiac geometry data 12, may be used to simulate corresponding BSP or ECG's 22 that would be observed at the patient's skin (such as waveforms or traces). In this way, a clinician can observe how different cardiac diseases or abnormalities might present themselves in a given patient.

Figure 2:
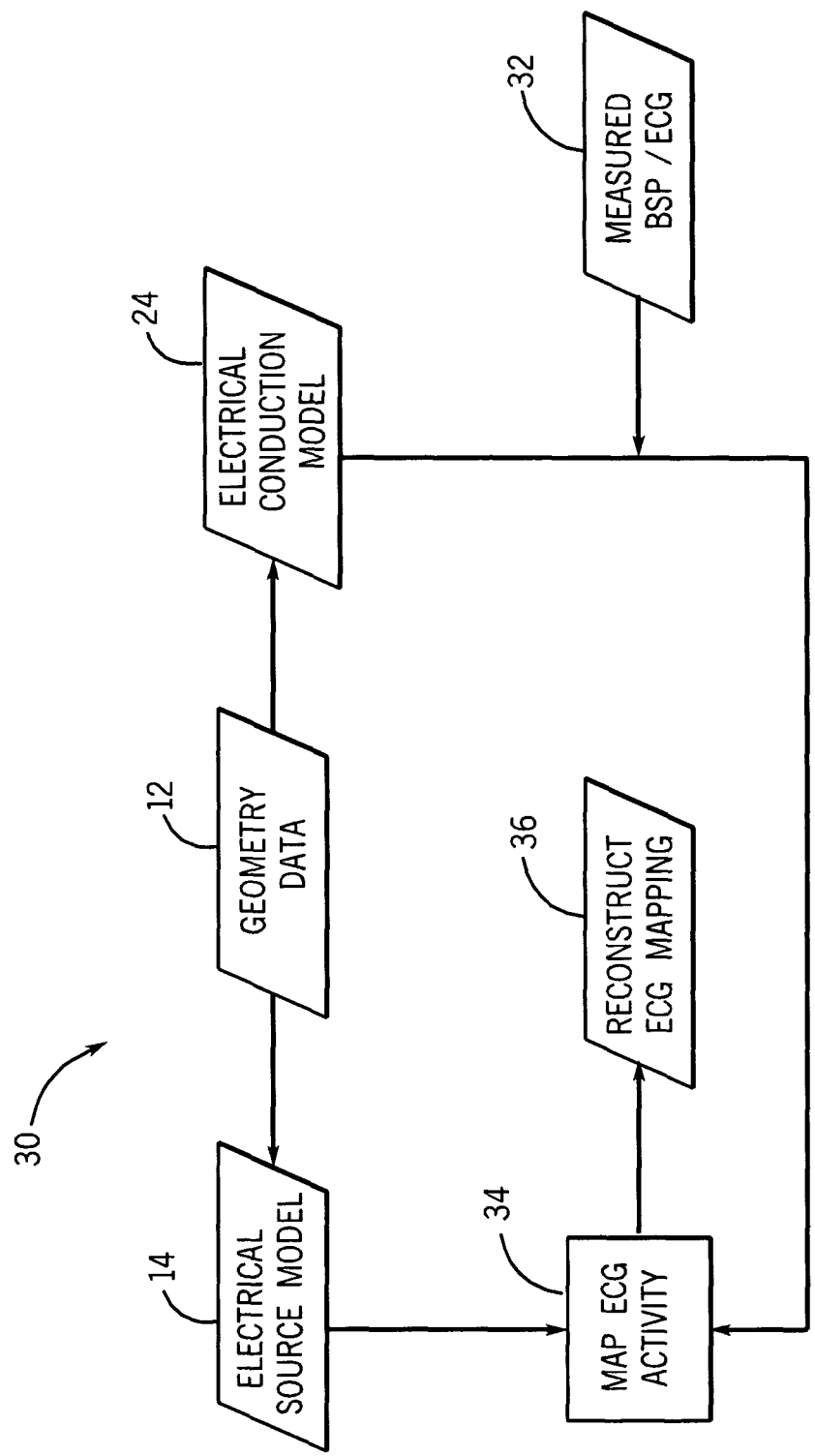
FIG. 2 illustrates an exemplary technique for generating a reconstructed ECG mapping onto a heart surface or volume, in accordance with one aspect of the present technique.

The preceding discussion describes the forward problem of determining what body surface potentials, Y, will be observed in a patient given certain cardiac electrophysiological activity, X, at the cardiac cellular level. In practice, however, a clinician is more likely to have Y, the body surface electrical potential at a given location, and want to solve for X, the electrophysiological activity of heart itself, than the other way around. In other words, a clinician is more likely to be interested in the inverse problem, solving for X and not Y. Turning now to FIG. 2, the inverse problem 30 is diagrammatically represented for discussion purposes. As depicted, in solving for the inverse problem, the geometry data 12, electrical source model 14, and electrical conduction model 24 are provided, as discussed above with regard to FIG. 1. In addition, the measured body surface potentials 32, in the form of BSP or ECG measurements, waveforms, or traces, are also provided.

Based on these inputs, a clinician may desire to map (block 34) the electrical potential activity of the heart in anatomical or cellular detail, such as by generating a reconstructed ECG mapping 36 of the heart in order to ascertain the heart condition or disease state, such as acute myocardial infarctions or ischemic zones, of a patient. In other words, given the measured body surface potentials, Y, and knowledge of the geometry of the heart 12 the clinician would like to know the electrophysiological activity, X, of each part or cell of the heart at a given time or times in the cardiac cycle. This problem, however, may be difficult to solve due to the multiple possible values of X that may exist for a given measured body surface potential, Y. Further, small measurement errors of the body surface potential or geometric errors (e.g., transfer matrix errors) may lead to unbounded perturbation in the surface potential solutions, making it difficult or impossible to solve for X.

Figure 3:
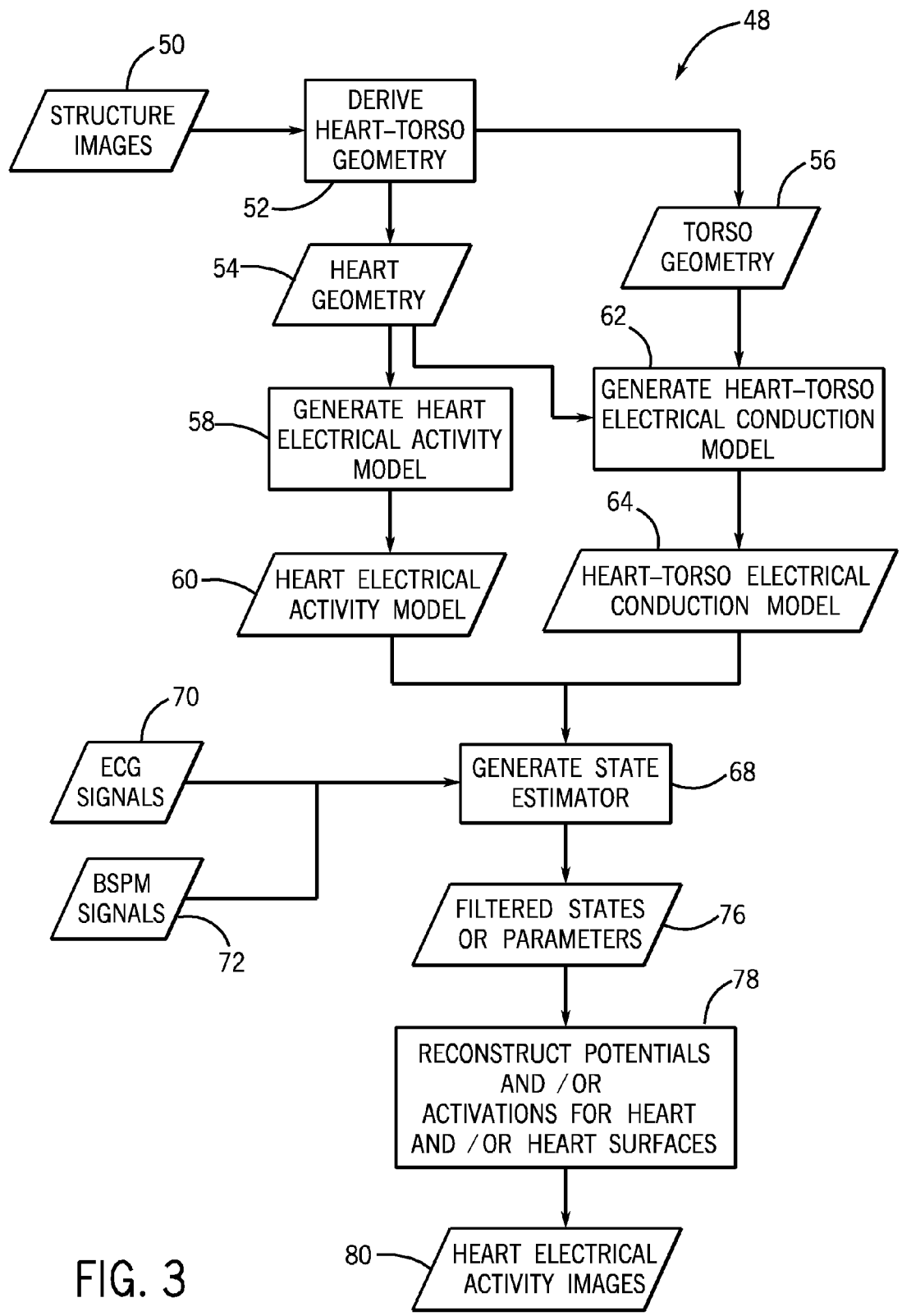
FIG. 3 is a flowchart depicting exemplary steps for generating heart electrical propagation images, in accordance with one aspect of the present technique.

Referring now to FIG. 3, an embodiment of the present technique (described generally by reference numeral 48) is described that addresses some or all of these issues. As depicted in FIG. 3, one or more structure images 50 of the anatomical region of interest are provided. For the purpose of this example, the one or more structure images 50 will be discussed as being of a heart and torso of a patient, though those of skill in the art will appreciate that structural images of other anatomical regions may also be provided in other implementations. The one or more structure images 50 may be derived using a suitable imaging modality, such as CT, MRI, ultrasound, tomosynthesis, and so forth, or a combination of such modalities.

In the present example, the three-dimensional heart geometry 54 and torso geometry 56 of the patient are derived (block 52) from the one or more structure images 50, such as CT, MRI, and/or ultrasound images. A quantitative heart electrical activity model 60 for the patient may be generated (block 58) or configured using the three-dimensional heart geometry 54. For example, in one embodiment, the heart electrical activity model 60 is generated at block 58 using bidomain theory or other suitable approaches. The heart electrical activity model 60 may be a volume source model, such as a model based on finite element or finite volume approaches, or a surface source, such as a model based on epicardial potential or double-layer approaches. Likewise, a quantitative heart-torso electrical or electromechanical conduction model 64 for the patient may be generated (block 62) or configured using the three-dimensional heart geometry 54 and torso geometry 56. For example, in one embodiment, the heart-torso electrical conduction model 64 is generated at block 62 using surface or volume methods, such as finite element, finite difference, boundary element, and/or finite volume approaches.

In the depicted implementation, the heart electrical activity model 60 and heart-torso electrical conduction model 64 are used to generate (block 68) a state estimator that is based on heart electrical activity and heart-torso conduction. As will be appreciated by those of ordinary skill in the art, the state being estimated by the state estimator in such an embodiment is the action potential of some or all of the myocardial cells. The parameters and/or states of the state estimator may then be adjusted online based on measured ECG and/or BSP activity. Heart electrical activity may then be calculated using the estimated states and/or model parameters.

For example, in one implementation, the heart electrical activity model 60 may characterize the electrical potentials, X, of each part or cell of the heart at a given time or times in the cardiac cycle based on a limited number of parameters. In such an example, the heart electrical activity model 60, X may be characterized such that:

$$X_{l,k}(n) = f(D_{l,k}, R_{l,k}, M_{l,k}, S_{l,k}, n) \quad (2)$$

where l denotes the cell number; k is the cycle number; n is the sample number; D is the depolarization time of the action potential curve; R is the repolarization time of the action potential curve; M is the depolarization magnitude of the action potential curve; and S is the repolarization slope of the action potential curve. Therefore, in such an example, instead of solving for X, one may solve for D, M, R, and S, or D, M, and R if S is assumed to be unchanged, i.e., one solves for the parameters characterizing X rather than X itself. For example, in one implementation, the values of D, R, and M may be estimated via virtual states as:

$$D_k = D_{k-1} + W^D_{k-1} \quad (3)$$

$$R_k = R_{k-1} + W^R_{k-1} \quad (4)$$

$$M_k = M_{k-1} + W^M_{k-1} \quad (5)$$

where $W^*_{k-1}$ is white noise. In such an approach, equation 1 may be represented as:

$$Y_k = \Lambda \cdot F(D_k, R_k, M_k). \quad (6)$$

As will be appreciated by those of ordinary skill in the art, equations (3), (4), (5), and (6) describe a typical nonlinear dynamic model and the characteristic parameters correspond to the "states" of the state estimator described herein.

In another example, the heart electrical activity model 60 may be characterized by equation (2) but with the characters D, R, M and S denoting different characteristics of the action potential, X, of each part or cell of the heart. For example, in this example, D is the depolarization time of the cellular action potential curve; R is the maximum conductance of an ionic channel associated with fast delayed potassium rectifier current; M is the scaling factor of an ionic channel associated with sodium-calcium exchanger current; and S is maximum conductance of an ionic channel associated with slow delayed potassium rectifier current. In such an example, the virtual states to be estimated may be also implemented by equation (3), (4), (5) and (6).

For instance, in the depicted embodiment, an extended Kalman filter is generated (block 68) and functions as the state estimator, i.e., the estimator of the action potentials, X, for some or all of the myocardial cells. In one implementation, the extended Kalman filter adapts the model parameters or states of the heart electrical activity model 60 to generate filtered states or parameters 76 in an online manner according to a cycle-by-cycle ECG measurement, i.e., ECG signal 70, and/or BSP measurement, i.e., BSP signal 72. In this manner, the heart electrical activity model 60 is leveraged to address the dynamic characteristics within a heart beat cycle.

Figure 4:
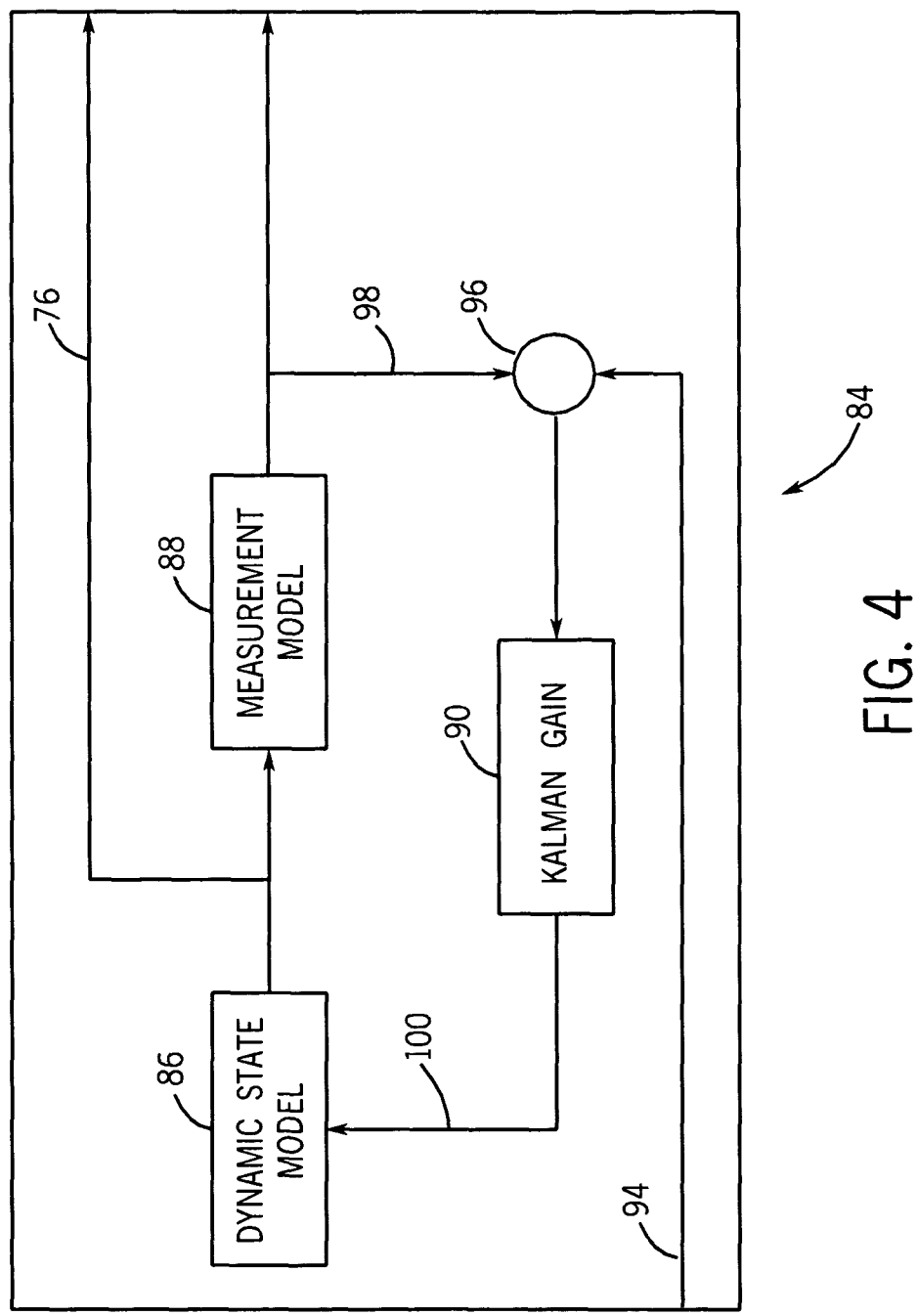
FIG. 4 depicts an example of an extended Kalman filter, in accordance with one aspect of the present technique.

An example of such an extended Kalman filter 84 is depicted in FIG. 4. The exemplary extended Kalman filter 84 depicted in FIG. 4 includes a dynamic state model 86, a measurement model 88, and a Kalman gain calculation 90. Current ECG and/or BSP measurements 94 are compared 96 with the estimates 98 of these measurements, and used to determine the adjustment 100 of the states and/or parameters 76 through modulation of Kalman gain 90 to the dynamic state model 86. The dynamic state model 86 outputs estimated states and/or parameters 76 that may be used to reconstruct the electrophysiological activity of the patient's heart. Likewise, the estimated states and/or parameters 76 may be used to update the ECG and/or BSP measurement through measurement model 88 as part of the overall filtering process.

In one such implementation of an extended Kalman filter the dynamics for the filter may be defined such that:

$$\delta(k+1) = \delta(k) + w(k), \text{ and} \quad (7)$$

$$y(k+1) = MAP(\delta(k+1)) + v(k), \text{ where} \quad (8)$$

$$E[w(k)w'(k)] = Q, \text{ and} \quad (9)$$

$$E[v(k)v'(k)] = R \quad (10)$$

where state $\delta = [D, R, M]$ is the characteristic parameter of cellular electrical potential, w(k) is white noise, MAP(·) is the model function as described in equation (6) to simulate the ECG and/or BSP measurement, E is the expectation operator, and the model is a random walk model. Based on these dynamics, the extended Kalman filter equations may be represented as:

$$\hat{\delta}(k+1|k+1) = \hat{\delta}(k+1|k) + K(k+1) \cdot \Delta(k+1), \text{ where} \quad (11)$$

$$\hat{\delta}(k+1|k) = \hat{\delta}(k|k) \quad (12)$$

$$\Delta(k+1) = ECG(k+1) - MAP(\hat{\delta}(k+1|k)) \quad (13)$$

$$C(k+1|k) = \left. \frac{\partial MAP}{\partial \delta} \right|_{\hat{\delta}(k+1|k)} \quad (14)$$

$$K(k+1) = P(k+1|k) \cdot C^T(k+1|k) \cdot [C(k+1|k) \cdot P(k+1|k) \cdot C^T(k+1|k) + R]^{-1} \quad (15)$$

$$P(k+1|k) = P(k|k) + Q, \text{ and} \quad (16)$$

$$P(k+1|k+1) = [I - K(k+1) \cdot C^T(k+1|k)] \cdot P(k+1|k) \quad (17)$$

In such an embodiment, the extended Kalman filter generated at block 68 may be used to estimate the parameters of the heart electrical activity model 60 so that the simulated ECG and/or BSP attributable to the model 60 and model 64 corresponds to or matches well with the measured ECG signal 70 and/or BSP signal 72. Therefore, in such an implementation, the electrical potentials, X, of each part or cell of the heart at a given time or times in the cardiac cycle is solved indirectly by calculating equation (2) using the dynamic adjustments to the heart electrical activity model parameters.

Returning now to FIG. 3, the filtered parameters or states 76 may be used to reconstruct (block 78) the potentials and/or activations across the whole heart or on the heart surfaces. For example, in one implementation, a signal processor, such as a processor or co-processor of a computer or workstation employed in image reconstruction, may execute routines performing such reconstructions. The reconstructed potentials and/or activations may be provided to a clinician to review the electrical potentials or activity at different portions or regions of the heart and at different times in the heart-beat cycles, thereby allowing the clinician to identify diseased or aberrant cardiac tissues, such as ischemia zones. Such reconstructions may take the form of heart electrical activity images 80.

For example, in one embodiment, the heart electrical activity images 80 are provided to the clinician as a rendered image or volume of the heart, such as may be derived or represented by three-dimensional structure images 50, with color-coding, gray-scaling, or other visual indications displayed that represent the electrical potentials, electrical activity, or other related characteristics derived from such activity or potentials of different regions or surfaces of the heart. Further in one such implementation, the heart electrical activity images 80 may be provided as a video or series of images or renderings of the heart that reflect the changes in the electrical activity or potentials of the heart regions or surfaces over time, such as over the course of a one or more heartbeats. For example, the clinician may be provided with a video of the heart where the surfaces or regions of the heart change color over time to reflect the electrical potential of the respective surface or region of the heart. In this manner, the heart electrical activity image 80 may be provided as a three-dimensional structural representation of the heart that is visually or color-coded to display electrical potential or activity information over time.

In one embodiment utilizing CT to generate the structural images 50 and a 64-lead ECG monitor to provide an ECG signal, a spatial resolution of 1-5 mm is anticipated for showing electrical potential and/or activity information with the rendered images or volumes. In such an embodiment, the resulting heart electrical activity images 80 may provide an electrocardiography mapping of the surface of the heart or of the entire heart (including the endocardium and epicardium) over time or in a dynamic fashion in response to real-time ECG and/or BSP measurements.

In another embodiment employing geometry data derived from structural images 50 generated using an MRI system, 576 heart nodes, i.e., locations on the heart, may be identified. An ECG monitor connected to leads disposed on a patient's torso may be used to measure ECG signals, which may be used to estimate the parameters D, R, and M described above for each heart node. A transfer matrix, A, may then be used to map body surface potentials from the simulated heart surface potentials using the estimated parameters, in accordance with equation 1 set forth above.

By dynamically characterizing heart electrical activity in the manner described, heart electrical activity can be effectively described using a limited number of parameters. Therefore, the number of independent variables (several model parameters as opposed to hundreds or thousands of potentials corresponding to electrical activity in one heart-beat cycle for each heart cell) may be dramatically reduced. Therefore, the present approach provides a more robust solution than previous techniques in solving X.

The preceding discussion addresses aspects of the present technique related to the processing of ECG or BSP data and image data. Exemplary systems that may be used in acquiring such data are described below. As will be appreciated by those of ordinary skill in the art, the following descriptions are merely intended to be generally illustrative of the types of systems that be used to generate surface potential and image data. Therefore, the following descriptions are not to be interpreted as an exhaustive presentation of how such systems might be configured or might function to acquire the described data. Nor are the following descriptions to be interpreted as an exhaustive presentation of the types of systems that might be employed in acquiring surface potential or image data that might be used in implementing the present technique as described above.

Figure 5:
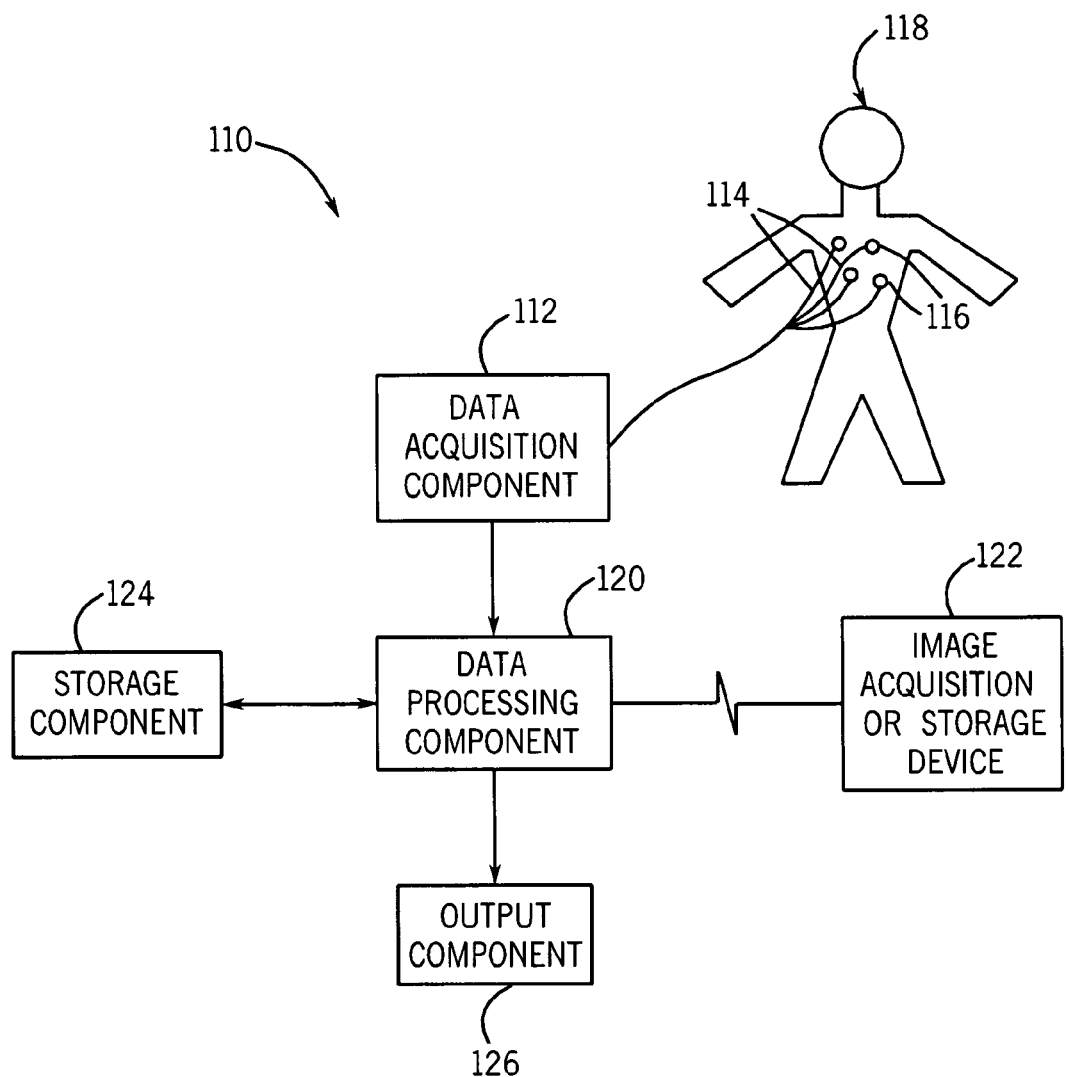
FIG. 5 depicts an exemplary ECG system for generating ECG data or body surface potential data in accordance with one aspect of the present technique.

Turning now to the example of an electrophysiology recording system, such as an ECG system 110 or a General Electric Cardiolab System® suitable for measuring body surface potentials, which may be used in conjunction with the present technique. The ECG system 110 may include a variety of components. For example, the ECG system 110 may include a data acquisition component 112 configured to receive electrical signals that convey the electrical activity of the heart, such as the depolarization and repolarization events associated with cardiac cell contraction. The electrical signals may be conducted to the data acquisition component 112 via electrical leads 114 terminating in contact pads 116 which are positioned on the torso of the patient 118. While four leads 114 and contact pads 116 are depicted in FIG. 5 for simplicity, other numbers of leads 114 and contact pads 116 may be employed. In particular, twelve lead ECG systems 110 are frequently employed in cardiac monitoring, though an N lead ECG system 110 may be employed in the present technique.

The ECG system 110 may also include a data processing component 120 configured to receive and/or process the electrical signals indicative of cardiac electrical activity. For example, the data processing component 120 may convert analog electrical signals to digital data, may analyze the data for recurring events or for events outside of a configured threshold, and/or may process the data for visual display, such as in a waveform, chart, graph, or text presentation. Similarly, the data processing component 120 may convert the ECG data into formats suitable for storage and/or display.

In addition, the data processing component 120 may perform the operations described herein using image data received from an image acquisition and/or storage device 122. For example, the image acquisition and/or storage device 122 could be an image acquisition system, such as a CT imaging system, and MRI, imaging system, an ultrasound imaging system, a C-arm or tomosynthesis imaging system, or other imaging modality suitable for acquiring three-dimensional image data of the anatomy of patient 118. Likewise, the image acquisition and/or storage device 122 may be a storage system or medium, such as a picture archiving and communication system (PACS) used to store and distribute such three-dimensional image data. As will be appreciated by those of ordinary skill in the art, the image acquisition and/or storage device 122 may be local to the ECG system 110 and, thus, in direct connection and communication with the ECG system 110. Alternatively, the image acquisition and/or storage device 122 may be remote from the ECG system 110 and in communication via a network or telecommunication link, such as a hospital local area network, the internet, or a virtual private network the processing of the electrical and image data may be accomplished by a suitable software package or similar computer executable routines configured to run on the data processing component 120 of the ECG system 110 (or corresponding electrophysiology recording system).

The processed ECG data, such as the heart electrical activity images 80 described above, may be transmitted to a storage component 124, such as one or more memory chips, magnetic drives, optical drives, and so forth, for short or long-term storage. The storage component 124 may be local or remote from the data processing component 120 and/or data acquisition component 112. For example, the storage component 124 may be a memory or storage device located on a computer network that is in communication with the data processing component 120. In the present context, the storage component 124 may also store programs and routines executed by the data processing component 120, including routines for implementing the present technique. For example, the storage component 124 may include an optical or magnetic disk or media upon which application instructions for performing the present technique are stored. In addition, the data processing component 120 may transmit the processed ECG data, such as the heart electrical activity images 80, to an output component 126, such as a printer or display. The heart electrical activity images 80, when displayed, may allow a clinician, such as a physician or electrophysiologist, to diagnose or determine the heart status accurately and non-invasively.

Figure 6:
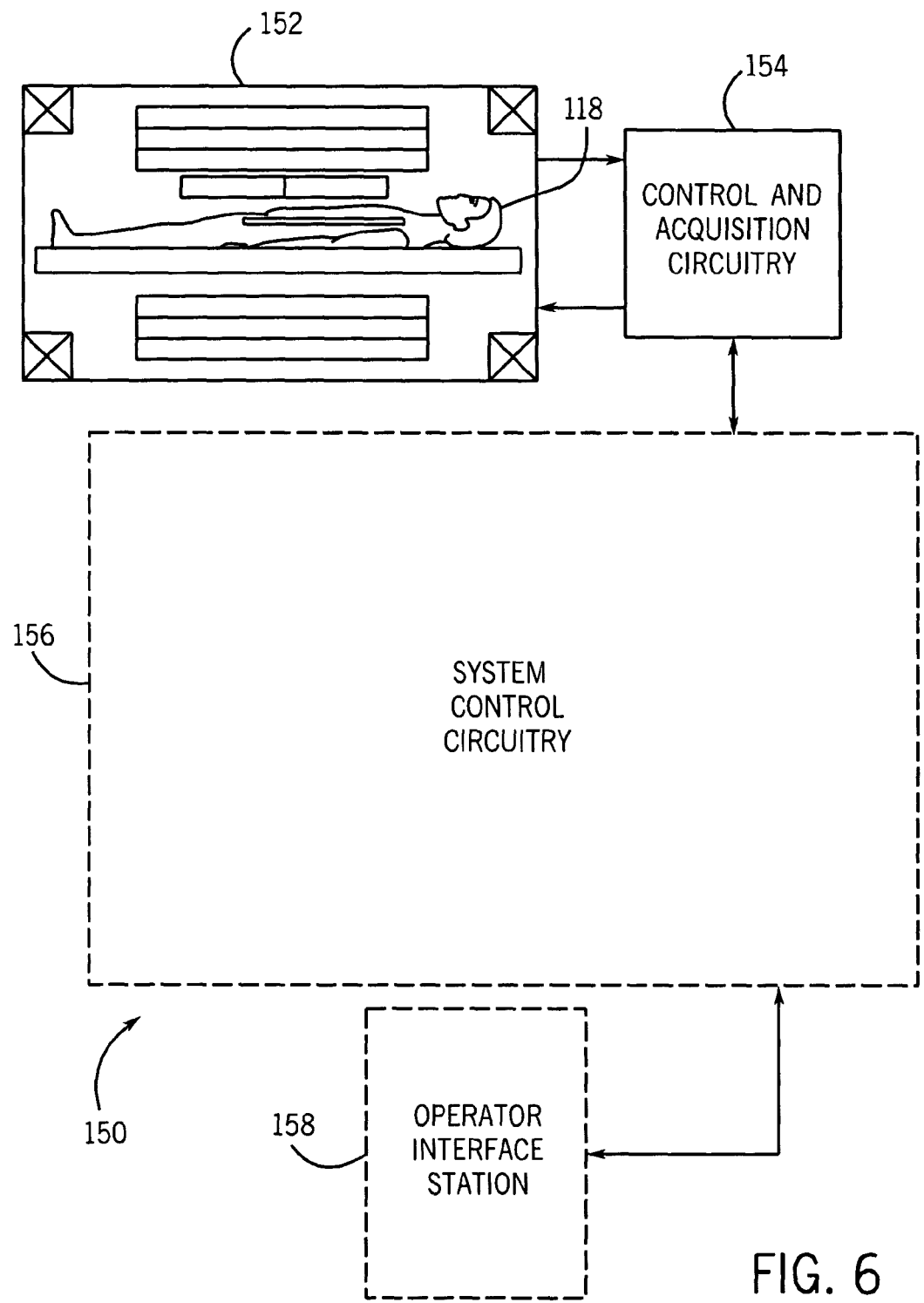
FIG. 6 depicts an exemplary magnetic resonance imaging system for generating structure or anatomical images, in accordance with one aspect of the present technique.

One example of an image acquisition and/or storage device 122 suitable for generating image data for use with the present technique is a magnetic resonance imaging system, designated generally by the reference numeral 150, as depicted in FIG. 6. As depicted, the magnetic resonance imaging system 150 includes a magnet assembly 152, control and acquisition circuitry 154, system controller circuitry 156, and an operator interface station 158. The magnet assembly 152, in turn, includes coil assemblies for selectively generating controlled magnetic fields used to excite gyromagnetic materials spin systems in a subject of interest. In particular, the magnet assembly 152 includes a primary coil, which will typically include a super conducting magnet coupled to a cryogenic refrigeration system. The primary coil generates a highly uniform magnetic field along a longitudinal axis of the magnet assembly. A transmit coil assembly consisting of a series of gradient coils and a transmit RF coil is provided for generating controllable gradient magnetic fields having desired orientations with respect to the patient 118. In particular, as will be appreciated by those skilled in the art, the transmit coil assembly produces fields in response to pulsed signals for selecting an image slice, orienting the image slice, and encoding excited gyromagnetic material spin systems within the slice to produce the desired image. A receiving coil assembly, such as a phased array coil assembly, according to one aspect of the invention, is provided for detecting emissions from gyromagnetic material spin systems during data acquisition phases of operation of the system.

In the embodiment illustrated in FIG. 6, the control and acquisition circuitry 154 includes coil control circuitry and signal processing circuitry. The coil control circuit receives pulse sequence descriptions from the system controller 156, such as through as interface circuit in the system controller 156. As will be appreciated by those skilled in the art, such pulse sequence descriptions generally include digitized data defining pulses for exciting the coils the transmit coil assembly during excitation and data acquisition phases of imaging. Fields generated by the coils of the transmit coil assembly excite the spin system within the patient 118 to cause emissions within the patient 118. Such emissions are detected by a receiving coil assembly and are filtered, amplified, and transmitted to signal processing circuitry. The signal processing circuitry may perform preliminary processing of the detected signals and/or amplification of the signals. Following such processing, the processed and/or amplified signals are transmitted to the interface circuitry for further processing.

In addition to the interface circuitry, the system controller 156 includes central processing circuitry, memory circuitry, and interface circuitry for communicating with the operator interface station 158. In general, the central processing circuitry, which will typically include a digital signal processor, a CPU or the like, as well as associated signal processing circuitry, commands excitation and data acquisition pulse sequences for the magnet assembly 152 and the control and acquisition circuitry 154 through the intermediary of the interface circuitry. The central processing circuitry also processes image data received via the interface circuitry, to perform 2D Fourier transforms to convert the acquired data from the time domain to the frequency domain, and to reconstruct the data into a meaningful image. The memory circuitry serves to save such data, as well as pulse sequence descriptions, configuration parameters, and so forth. The interface circuitry permits the system controller 156 to receive and transmit configuration parameters, image protocol and command instructions, and so forth.

The operator interface station 158 includes one or more input devices, along with one or more display or output devices. In a typical application, the input devices will include a conventional operator keyboard, or other operator input devices for selecting image types, image slice orientations, configuration parameters, and so forth. The display/output devices will typically include a computer monitor for displaying the operator selections, as well as for viewing scanned and reconstructed images. Such devices may also include printers or other peripherals for reproducing hard copies of the reconstructed images.

Figure 7:
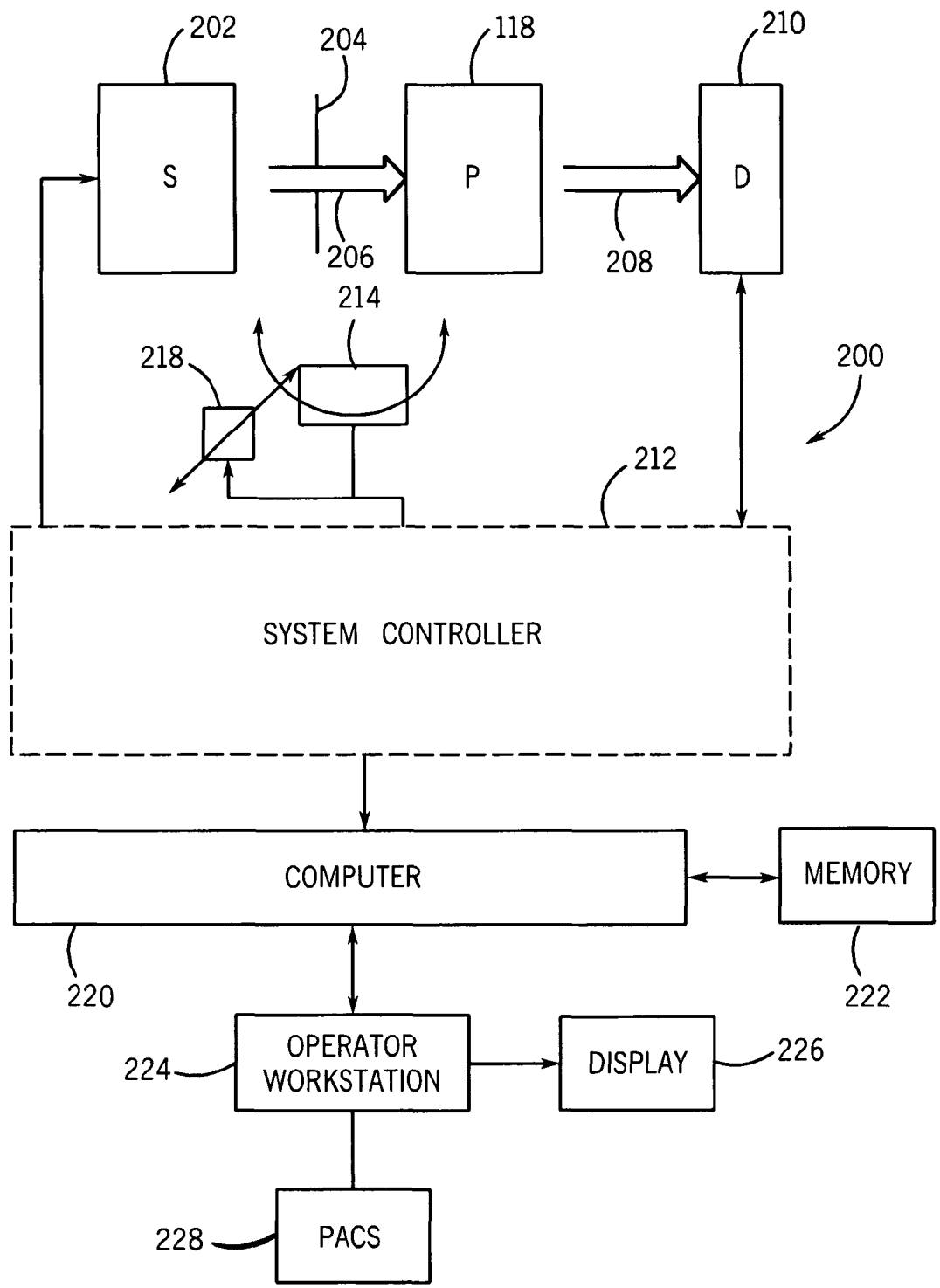
FIG. 7 depicts an exemplary computed tomography imaging system for generating structure or anatomical images, in accordance with one aspect of the present technique.

Another example of an image acquisition and/or storage device 122 suitable for generating image data for use with the present technique is a computed tomography imaging system, designated generally by the reference numeral 200, as depicted in FIG. 7. The computed tomography (CT) imaging system 200 is designed to acquire X-ray projection data, to reconstruct the projection data into an image, and to process the image data for display and analysis in accordance with the present technique.

In the embodiment illustrated in FIG. 7, CT imaging system 200 includes a source 202 of X-ray radiation, such as one or more X-ray tubes or solid state X-ray source having one or more field emitters. The X-ray source 202 may be positioned proximate to a collimator 204 consisting of a collimating region, such as lead or tungsten shutters, for each emission point of the source 202. The collimator 204 typically defines the size and shape of one or more streams of radiation 206 that pass into a region in which a subject, such as a human patient 118, is positioned. An attenuated portion of the radiation 208 passes through the subject, which provides the attenuation, and impacts a detector array, represented generally at reference numeral 210.

Each detector element of the detector 210, when impacted by an X-ray, produces an electrical signal that represents the intensity of the X-ray beam at the position of the element during the time the beam strikes the detector 210. Typically, signals are acquired at a variety of view angle positions around the subject of interest so that a plurality of radiographic views may be collected. These signals are acquired and processed to reconstruct an image of the features within the subject.

The X-ray source 202 is controlled by a system controller 212, which furnishes power, focal spot location, control signals and so forth for CT examination sequences. Moreover, the detector 210 is coupled to the system controller 212, which commands acquisition of the signals generated in the detector 210. The system controller 212 may also execute various signal processing and filtration functions, such as for initial adjustment of dynamic ranges, interleaving of digital image data, and so forth. In general, system controller 212 commands operation of the imaging system 200 to execute examination protocols and to process acquired data. In the present context, system controller 212 also includes signal processing circuitry, typically based upon a general purpose or application-specific digital computer, and associated memory circuitry.

In the embodiment illustrated in FIG. 7, system controller 212 may control the movement of a rotational subsystem 214 and linear positioning subsystem 218 via a motor controller. In imaging system 200 in which the source 202 and/or the detector 210 may be rotated, the rotational subsystem 214 may rotate the X-ray source 202, the collimator 204, and/or the detector 210 through one or multiple turns around the patient 118. It should be noted that the rotational subsystem 214 might include a gantry. The linear positioning subsystem 218 enables the patient 118, or more specifically a patient table, to be displaced linearly. Thus, the patient table may be linearly moved within the gantry to generate images of particular areas of the patient 118, such as the heart.

As will be appreciated by those skilled in the art, the source 202 of radiation may be controlled by an X-ray controller disposed within the system controller 212. Further, the system controller 212 may comprise a data acquisition system that receives data collected by readout electronics of the detector 210. In particular, the data acquisition system typically receives sampled analog signals from the detector 210 and converts the data to digital signals for subsequent processing by a computer 220.

The computer 220 is typically coupled to the system controller 212. The data collected by the data acquisition system may be transmitted to the computer 220 for subsequent processing and reconstruction. For example, the data collected from the detector 210 may undergo pre-processing and calibration at the data acquisition system and/or the computer 220. The processed data, commonly called projections, may then be processed to formulate an image of the scanned area. Once reconstructed, the image produced by the CT system of FIG. 7 reveals an internal region of interest of the patient 118 which may be used in accordance with the present technique.

The computer 220 may also be adapted to control features enabled by the system controller 212, i.e., scanning operations and data acquisition and may comprise or communicate with a memory 222 that can store data processed by the computer 220 or data to be processed by the computer 220. Furthermore, the computer 220 may be configured to receive commands and scanning parameters from an operator via an operator workstation 224 which may be equipped with a keyboard and/or other input devices. An operator may thereby control the CT system 200 via the operator workstation 224. A display 226 coupled to the operator workstation 224 may be utilized to observe a reconstructed image. Further, the operator workstation 224 may also be coupled to a picture archiving and communications system (PACS) 228.

It should be appreciated that, while the preceding discussion related different imaging systems that might be suitable for providing image data to an electrophysiology recording system, such as ECG system 110, for implementing the present technique for generating heart activity electrical images 80, other implementations are also feasible. For example, the additional functionality described herein may instead be provided as part of an imaging system, such as the MRI imaging system 150, the CT imaging system 200, or an ultrasound imaging system. For example, additional hardware and/or processing circuitry may be provided as part of the system control circuitry 156 and/or operator interface station 158 of the MRI system 150, as part of the system controller 212, computer 220, and/or operator workstation 224 of the CT imaging system 200, or as part of the corresponding data processing components of a respective ultrasound imaging system to generate heart activity electrical images 80. Such hardware may provide for the acquisition of ECG or BSP data at the corresponding imaging system.

A suitable software package or similar computer executable routines may be provided on the storage and processing components of the respective imaging system to process the acquired three-dimensional image data and the ECG or BSP electrical data, as described herein, and to thereby generate useful heart electrical activity images 80 or other data presentations that leverage both the available electrical and image data. Such a combined electrical-imaging system provides advantages in evaluating heart health, such as by reducing false positive and/or false negative diagnoses related to acute myocardial infarction.

While only certain features of the invention have been illustrated and described herein, many modifications and changes will occur to those skilled in the art. It is, therefore, to be understood that the appended claims are intended to cover all such modifications and changes as fall within the true spirit of the invention.

The invention claimed is:

1. A method for determining cellular electrical potentials, comprising:
    deriving an electrical source model and an electrical conduction model based on one or more structural images, wherein the electrical source model and the electrical conduction model are not updated based on subsequent processes;
    generating a state estimator using at least the electrical source model and the electrical conduction model;
    adjusting one or more parameters or states of the state estimator based on at least one of a measured electrocardiographic signal or a measured body-surface-potential signal; and
    determining the electrical potential of one or more cells based on the one or more adjusted parameters or states.

2. The method of claim 1, wherein the electrical source model comprises at least one of a cellular electrical or electromechanical model and/or a heart electrical or electromechanical propagation model.

3. The method of claim 1, wherein the electrical conduction model comprises a heart-torso electrical or electromechanical conduction model.

4. The method of claim 1, wherein the state estimator comprises an extended Kalman filter that generates filtered states based on a cycle-by-cycle ECG measurement.

5. The method of claim 1, wherein the one or more cells are myocardial cells.

6. The method of claim 1, wherein the one or more cells form a surface or a volume of an internal organ.

7. The method of claim 1, comprising:
    deriving a heart geometry and a torso geometry from the one or more structural images, wherein the one or more structural images comprise three-dimensional images;
    generating the electrical source model based at least on the heart geometry; and
    generating the electrical conduction model based at least on the torso geometry.

8. The method of claim 7, wherein the one or more three-dimensional images are acquired using at least one of a computed tomography imaging system, a magnetic resonance imaging system, and ultrasound imaging system, or a tomosynthesis imaging system.

9. The method of claim 1, comprising:
generating one or more representations of an organ comprising the one or more cells, wherein the electrical potential or a deriving characteristic of the one or more cells is visually indicated.

10. The method of claim 9, wherein the organ comprises a heart.

11. The method of claim 9, wherein the electrical potential or a deriving characteristic of the one or more cells is visually indicated by color or gray-scale.

12. The method of claim 9, wherein the one or more representations comprises a video or a series of volumetric images depicting changes in the electrical potential or a deriving characteristic of the one or more cells over time.

13. The method of claim 9, wherein the one or more representations have a resolution between approximately 1 mm to approximately 5 mm.

14. One or more non-transitory computer-readable media having application instructions for determining cellular electrical potentials encoded thereon, wherein the instructions, when processed:
derive an electrical source model and an electrical conduction model based on one or more structural images, wherein the electrical source model and the electrical conduction model are not updated based on subsequent processes;
generate a state estimator using at least the electrical source model and the electrical conduction model;
adjust one or more parameters or states of the state estimator based on at least one of a measured electrocardiographic signal or a measured body-surface-potential signal; and
determine the electrical potential of one or more cells based on the one or more adjusted parameters or states.

15. The one or more non-transitory computer-readable media of claim 14, wherein the instructions that generate the state estimator when processed use at least one of a cellular electrical or electromechanical model and/or a heart electrical or electromechanical propagation model as the electrical source model and use a heart-torso electrical or electromechanical conduction model as the electrical conduction model.

16. The one or more non-transitory computer-readable media of claim 14, wherein the one or more structural images comprise three-dimensional images.

17. The one or more non-transitory computer-readable media of claim 14, wherein the instructions that determine the electrical potential of one or more cells when processed determine the electrical potential of one or more myocardial cells.

18. The one or more non-transitory computer-readable media of claim 14, wherein the instructions that generate the state estimator when processed generate an extended Kalman filter that generates filtered states based on a cycle-by-cycle ECG measurement.

19. The one or more non-transitory computer-readable media of claim 14, wherein the application instructions, when processed, also:
derive at least a heart geometry and a torso geometry from the one or more structural images, wherein the one or more structural images comprise three-dimensional images;
generate the electrical source model based at least on the heart geometry; and
generate the electrical conduction model based at least on the torso geometry.

20. The one or more non-transitory computer-readable media of claim 14, wherein the application instructions, when processed, also generate one or more representations of an organ comprising the one or more cells, wherein the electrical potential or its deriving characteristic of the one or more cells is visually indicated.

21. The one or more non-transitory computer-readable media of claim 20, wherein the instructions that generate the one or more representations when processed generate a video or a series of volumetric images depicting changes in the electrical potential or its deriving characteristic of the one or more cells over time.

22. A diagnostic system, comprising:
a data processing component configured to derive an electrical source model and an electrical conduction model based on one or more structural images, wherein the electrical source model and the electrical conduction model are not updated based on subsequent processes; to generate a state estimator using at least an electrical source model and an electrical conduction model, to adjust one or more parameters or states of the state estimator based on at least one of a measured electrocardiographic signal or a measured body-surface-potential signal, and to determine the electrical potential of one or more cells based on the one or more adjusted parameters or states.

23. The diagnostic system of claim 22, comprising a data acquisition component configured to acquire the measured electrocardiographic signal or the measured body-surface-potential signal via one or more leads.

24. The diagnostic system of claim 22, comprising an image acquisition and/or storage device configured to provide the one or more structural images from which at least one of the electrical source model or the electrical conduction model are derived.

25. The diagnostic system of claim 24, wherein the image acquisition and/or storage device comprises a computed tomography imaging system, a magnetic resonance imaging system, an ultrasound imaging system, a tomosynthesis imaging system, or a picture archiving and communication system.

26. The diagnostic system of claim 22, wherein the data processing component is configured to generate an extended Kalman filter as the state estimator, wherein the extended Kalman filter generates filtered states based on a cycle-by-cycle ECG measurement.

27. The diagnostic system of claim 22, wherein the data processing component is configured to derive at least a heart geometry and a torso geometry from the one or more structural images, wherein the one or more structural images comprise three-dimensional images, to generate the electrical source model based at least on the heart geometry, and to generate the electrical conduction model based at least on the torso geometry.

28. The diagnostic system of claim 22, wherein the data processing component is configured to generate one or more representations of an organ comprising the one or more cells, wherein the electrical potential or its deriving characteristic of the one or more cells is visually indicated.

* * * * *